(12) United States Patent
Thalacker et al.

(10) Patent No.: US 7,700,668 B2
(45) Date of Patent: Apr. 20, 2010

(54) ADHESIVE COMPOSITION WITH DECREASED POLARITY UPON POLYMERIZATION

(75) Inventors: Christoph Thalacker, Weilheim (DE); Reinhold Hecht, Kaufering (DE); Gioacchino Raia, Tuerkenfeld (DE); Manfred Ludsteck, Geretsried (DE); Karsten Dede, Landsberg (DE)

(73) Assignee: 3M ESPE AG, Seefeld (DE)

( * ) Notice: Subject to any disclaimer, the term of this patent is extended or adjusted under 35 U.S.C. 154(b) by 631 days.

(21) Appl. No.: 10/564,101

(22) PCT Filed: Jul. 14, 2004

(86) PCT No.: PCT/EP2004/007745

§ 371 (c)(1),
(2), (4) Date: Jun. 13, 2006

(87) PCT Pub. No.: WO2005/004819

PCT Pub. Date: Jan. 20, 2005

(65) Prior Publication Data
US 2006/0270751 A1   Nov. 30, 2006

(30) Foreign Application Priority Data
Jul. 14, 2003   (EP)   .................. 03015965

(51) Int. Cl.
A61K 6/083   (2006.01)

(52) U.S. Cl. ............. 523/116; 523/118; 433/228.1

(58) Field of Classification Search ................. 523/116, 523/118
See application file for complete search history.

(56) References Cited

U.S. PATENT DOCUMENTS

| | | | |
|---|---|---|---|
| 3,855,364 A * | 12/1974 | Steckler ............ 558/114 |
| 4,503,169 A | 3/1985 | Randklev |
| 4,695,251 A | 9/1987 | Randklev |
| 4,719,149 A | 1/1988 | Aasen et al. |
| 5,256,447 A | 10/1993 | Oxman et al. |
| 5,264,513 A | 11/1993 | Ikemura et al. |
| 5,525,648 A | 6/1996 | Aasen et al. |
| 5,554,669 A | 9/1996 | Nakabayashi et al. |
| 5,925,690 A | 7/1999 | Fuchigami et al. |
| 5,998,495 A | 12/1999 | Oxman et al. |
| 6,025,406 A | 2/2000 | Oxman et al. |
| 6,043,295 A | 3/2000 | Oxman et al. |
| 6,084,004 A | 7/2000 | Weinmann et al. |
| 6,187,833 B1 | 2/2001 | Oxman et al. |
| 6,191,190 B1 | 2/2001 | Blackwell et al. |
| 6,245,872 B1 | 6/2001 | Frey et al. |
| 6,254,828 B1 | 7/2001 | LaCount |
| 6,387,982 B1 | 5/2002 | Blackwell |
| 6,444,725 B1 | 9/2002 | Trom et al. |
| 2003/0166737 A1 | 9/2003 | Dede et al. |
| 2005/0196726 A1 * | 9/2005 | Fischer ............ 433/224 |

FOREIGN PATENT DOCUMENTS

| | | |
|---|---|---|
| DE | 2711234 A | 9/1977 |
| DE | 19918974 A | 12/1999 |
| DE | 19961342 A1 | 7/2001 |
| EP | 0074708 B | 3/1983 |
| EP | 0323120 A1 | 7/1989 |
| EP | 0712622 A | 5/1996 |
| EP | 0842651 A | 5/1998 |
| EP | 0895943 B1 | 2/1999 |
| EP | 0937448 A2 | 8/1999 |
| EP | 1051961 A | 11/2000 |
| WO | WO 98/47046 A1 | 10/1998 |
| WO | WO 98/47047 A1 | 10/1998 |
| WO | WO 01/10388 A1 | 2/2001 |
| WO | WO 01/30305 A1 | 5/2001 |
| WO | WO 01/30306 A1 | 5/2001 |
| WO | WO 01/30307 A1 | 5/2001 |
| WO | WO 01/44338 A1 | 6/2001 |
| WO | WO 01/51540 A2 | 7/2001 |
| WO | WO 01/58869 A2 | 8/2001 |
| WO | WO 02/38468 A1 | 5/2002 |
| WO | WO 02/066535 A1 | 8/2002 |

OTHER PUBLICATIONS

Fouassier, J.P., Photoinitiation, Photo-Polymerization, and Photocuring, Hanser Publishers, Munich, Vienna, New York, 1995.

Fouassier, J.P., J. F. Rabek (eds), Radiation Curing in Polymer Science and Technology, vol. II, Elsevier Applied Science, London, New Yori, 1993.

* cited by examiner

Primary Examiner—Tae H Yoon

(57) ABSTRACT

The invention relates to adhesive compositions that exhibit a significant decrease in polarity upon polymerization. More specifically, it relates to curable self etching dental adhesive compositions that can be applied to the tooth hard substance in one step and exhibit this decrease in polarity upon curing. In this respect a formulation is provided combining phosphoric acid esters bearing substituents with one ethylenically unsaturated moiety on the phosphorus atom and phosphoric acid esters bearing substituents with two or more ethylenically unsaturated moieties on the phosphorus atom.

13 Claims, No Drawings

ADHESIVE COMPOSITION WITH DECREASED POLARITY UPON POLYMERIZATION

The invention relates to adhesive compositions that exhibit a significant decrease in polarity upon polymerization. More specifically, it relates to curable self-etching dental adhesive compositions that can be applied to the tooth hard substance in one step and exhibit an decrease in polarity upon curing.

This can be reached by a formulation combining phosphoric acid esters bearing substituents with one ethylenically unsaturated moiety on the phosphorus atom and phosphoric acid esters bearing substituents with two or more ethylenically unsaturated moieties on the phosphorus atom.

The invention also relates to hydrophobic adhesive compositions with improved film forming properties on hydrophilic substrates. More specifically, it relates to curable self-etching hydrophobic dental adhesive compositions that can be applied in one step with improved film forming properties on dental hard tissue.

Without impairing the hydrophobic character of the formulation, this can be reached by adding optionally polymerizable monomers, polymers and/or prepolymers.

Dental compositions comprising ethylenically unsaturated phosphoric acid derivatives are disclosed in numerous documents.

EP 0 712 622 B1 discloses dental primer pre-treatment compositions having a monomer with a phosphorous group, a carboxylic acid containing monomer, and water as main components. As examples of the phosphoric acid group-containing monomer phosphoric acid monoesters, diesters and pyrophosphoric acid ester derivatives are suggested.

U.S. Pat. No. 5,256,447 discloses an adhesive composition comprising an ethylenically unsaturated phosphorylated compound, a carboxylic acid functional polymer, and a polymerization initiator, and optionally comprising a particulate metallic filler.

EP 0 074 708 B1 discloses an adhesive composition comprising a phosphoric acid derivative either with one group directly bound to the P atom which is monofunctional regarding methacryloxy, or with one group directly bonded to the P atom which is difunctional regarding methacryloxy. For the monofunctional derivatives, the methacryloxy residues are connected to the phosphorous atom via an alkylene group with at least 5 carbon atoms.

EP 1 051 961 A1 discloses a bonding composition for dental use comprising a mixture of acid group-having polymerizable compound, a water-soluble film forming agent (e.g. HEMA), water, and a curing agent.

U.S. Pat. No. 5,264,513 A discloses a primer composition comprising water, a compound having hydroxyl group and polymerizable group (e.g., HEMA), a compound having acidic group and polymerizable unsaturated group (e.g., bis[2-(meth)acryloxyethyl]phosphoric acid, but also thiophosphoric acid derivatives and compounds with anhydride residues).

WO 01/10388 A1 discloses adhesive compositions in which, as cationic initiator systems, ethylenically unsaturated phosphoric acid esters are disclosed comprising compounds like ethylenically unsaturated phosphoric acid derivatives, comprising, on the one hand, derivatives having groups directly bonded to the phosphorous atom which are monofunctional regarding methacryloxy and, on the other hand, derivatives having groups directly bonded to the phosphorous atom which are difunctional regarding methacryloxy.

EP 0 842 651 A1 discloses a primer for preparing a surface of a tooth for adhering to a composite filling material which comprises, among others, mixtures of ethylenically unsaturated phosphoric acid derivatives. However, only compounds are disclosed having groups being directly bonded to the phosphorous atom which have one ethylenically unsaturated group.

U.S. Pat. No. 4,719,149 (3M) discloses dental primer compositions containing an acid or water-soluble film former, which is soluble in water to at least 5 weight percent.

U.S. Pat. No. 5,525,648 discloses dental primer compositions containing a film former which contains a polymer, and which is water-dispersible to at least 5 weight percent. The polymers preferably contain functional groups that have an affinity for the hard tissue, such as β-dicarbonyl groups and carboxylic acid groups.

U.S. Pat. No. 6,191,190 B1 discloses a bonding composition for dental use comprising a film forming agent which is water-soluble to at least 5 weight percent.

U.S. Pat. No. 6,387,982 B1 discloses polymerizable surfactants having polyether chains that can be linked via a urethane moiety to a polymerizable group.

U.S. Pat. No. 6,191,190 B1 discloses a method and composition for adhering to tooth structure, which can contain vinyl urethane or urethane-acrylate prepolymers.

U.S. Pat. No. 5,554,669 discloses an emulsion of polymer having (meth)acrylate unit and adhesive compositions containing the emulsion. The polymer comprises a) a recurring unit derived from a (meth)acrylate and b) a recurring unit derived from a vinyl compound having a sulfonate moiety.

Self-etching dental adhesives of the state of the art contain usually at least one singly or repeatedly ethylenically unsaturated phosphoric acid ester as adhesion promoter. Owing to the synthetic procedure and starting materials, some of these adhesion promoters are rather hydrophilic and therefore well suited for wetting and etching dental hard tissue. On the other hand, they are more susceptible to hydrolysis and water uptake in the oral environment than formulations containing less polar monomers. Typically, these compounds bear substituents with one ethylenically unsaturated moiety on the phosphorus atom.

Other adhesion promoters bearing substituents with two or more ethylenically unsaturated moieties are less polar than those mentioned above and exhibit a higher degree of functionality. However, often the etching ability is not sufficient.

Known self-etching one-step dental adhesives ("sixth generation adhesives") consist mainly of rather hydrophilic ethylenically unsaturated phosphoric acid esters, which are suited for wetting and etching dental hard tissue. If one attempts to formulate less polar self-etching one-step dental adhesives, in some cases dewetting phenomena are observed which result in the formation of small droplets instead of a homogeneous film of bonding agent.

It is thus an object of the present invention to avoid one or more of the problems mentioned above.

A further object is to provide a dental composition with improved properties, especially a dental composition with sufficient etching properties and decreased hydrophilicity that can be applied in one step.

A further object is to provide a dental composition with improved film forming properties on hydrophilic substrates.

A further object is to provide a dental composition which can be used for the adhesive securing of materials based on methacrylates and/or epoxies to tooth or bones.

Still a further object is to provide a dental composition which can be used as a pit and fissure sealant or a desensitizer.

Another object is to provide a dental composition showing a low water uptake.

One or more objects can be achieved by providing a dental composition as described in the text below.

In this respect a formulation is provided combining phosphoric acid esters bearing substituents with one ethylenically unsaturated moiety on the phosphorus atom and phosphoric acid esters bearing substituents with two or more (e.g. 3, 4 or 5) ethylenically unsaturated moieties on the phosphorus atom.

Adding prepolymers, especially urethane (meth)acrylate prepolymers to the composition mentioned above helps to improve the film forming properties of the composition.

In a preferred embodiment the invention therefore relates to a curable dental composition, comprising a) one or a mixture of phosphoric acid esters bearing substituents with one ethylenically unsaturated moiety on the phosphorus atom according to formula (I),

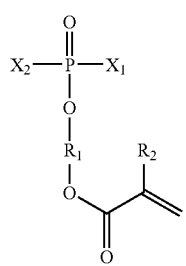
(I)

wherein $R_1$=(i) alkylene having 1 to 4 carbon atoms, (ii) or a bivalent organic group having 1 to 4 carbon atoms composed of two or more hydrocarbon residues bonded to one another by one or more ether or thioether linkages, (iii) or aryl, each optionally substituted with OH;

wherein $R_2$=H, $CH_3$;

wherein $X_1$=OH or halogen; and wherein $X_2$=$X_1$ or —O—$R_1$—OOC—$CR_2$=$CH_2$, b) one or a mixture of phosphoric acid esters bearing substituents with two or more ethylenically unsaturated moieties on the phosphorus atom according to formula (II),

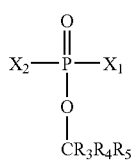
(II)

wherein $R_3$, $R_4$, and $R_5$=(i) H, (ii) linear or branched alkyl having 1 to 4 carbon atoms, optionally substituted with OH, (iii) aryl, optionally substituted with OH, (iv) organic group having 5 to 15 carbon atoms composed of 2 to 6 saturated or ethylenically unsaturated hydrocarbon residues bonded to one another by one or more ether, thioether, ester, thioester, thiocarbonyl, amide, urethane, carbonyl and/or sulfonyl linkages, each optionally substituted with OH, wherein at least 2 of the groups $R_3$, $R_4$, and $R_5$ comprise at least 1 group according to formula (III)

or at least 1 of the groups $R_3$, $R_4$, and $R_5$ comprises at least 2 groups according to formula (III)

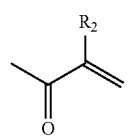
(III)

and wherein $X_2$=$X_1$ or —O—$CR_3R_4R_5$ or —O—$R_1$—OOC—$CR_2$=$CH_2$, (b) being usually present in an amount of about 1 to about 500 parts by weight based on about 100 parts by weight of (a), preferably about 100 to about 300 parts by weight based on about 100 parts by weight of (a), more preferably about 150 to about 250 parts by weight based on about 100 parts by weight of (a).

The total amount of (a) and (b) in the composition is usually in the range of about 10 to about 90 parts by weight, or in the range of about 20 to about 80 parts by weight, or in the range of about 30 to about 70 parts by weight, c) initiators in an amount of about 0.1 to about 20 parts by weight, or about 0.2 to about 10 parts by weight, or about 0.3 to about 5 parts by weight, d) stabilizers in an amount of about 0 to about 5 parts by weight, or about 0.001 to about 2 parts by weight, or about 0.01 to about 1 parts by weight, e) unsaturated monomers in an amount of about 5 to about 90 parts by weight, or about 10 to about 80 parts by weight, or about 20 to about 70 parts by weight, f) optionally unsaturated polymers and/or prepolymers in an amount of about 0 to about 30 parts by weight, or about 1 to about 20 parts by weight, or about 2 to about 15 parts by weight, g) optionally a solvent in an amount of about 0 to about 20 parts by weight, or about 1 to about 15 parts by weight, or about 3 to about 10 parts by weight, h) optionally a fluoride releasing agent in an amount of about 0 to about parts by weight, preferably about 0.2 to about 10 parts by weight, or about 0.3 to about 5 parts by weight, i) optionally a non reactive inorganic filler in an amount of about 0 to about 70 parts by weight, or about 5 to about 60 parts by weight, or about 10 to about 50 parts by weight, j) optionally a photobleachable colorant in an amount of about 0 to about 5 parts by weight, or about 0.05 to about 3 parts by weight, or about 0.1 to about 2 parts by weight.

The optional components mentioned above might be present in the composition alone or in combination with the other optional components.

The terms "comprise" and "contain" within the meaning of the invention introduce a non exhaustive list of features. Likewise, the word "one" is to be understood in the sense of "at least one".

The term "on the phosphorus atom" means that the ethylenically unsaturated moiety/moieties is/are present in one of the substituents bonded to the phosphorus atom. The preferred ethylenically unsaturated moieties are represented by formula (III).

That is component (b) of the inventive dental composition comprises at least two ethylenically unsaturated moieties within one substituent or branch bonded to the phosphoric acid ester.

Without wishing to be bound to any particular mechanism, it is believed that using a combination of one or a mixture of phosphoric acid esters bearing substituents with one ethylenically unsaturated moiety on the phosphorus atom preferably according to formula (I) and one or a mixture of phosphoric acid esters bearing substituents with two or more ethylenically unsaturated moieties on the phosphorus atom preferably according to formula (II), the composition obtained shows a decrease in polarity upon curing as well as good adhesion properties.

Moreover, without wishing to be bound to any particular mechanism, it is assumed that sufficient etching is provided by component (a), whereas the higher functionality and the less polar character of component (b) allows for a higher degree of crosslinking and leads to a significant decrease in polarity upon polymerization.

Furthermore, without wishing to be bound to any particular mechanism, it is believed that the addition of urethane prepolymers leads to improved film forming properties on hydrophilic substrates without increasing the polarity of the composition, as the urethane prepolymers preferably do not contain any hydroxy, acidic, or ionic groups.

The water uptake measured after having immersed the composition for 5 h in water of 37° C. as described in the examples below can be as low as about 5% by weight or as low as about 4% by weight, sometimes lower.

It can also be advantageous if the dental composition does not only have a low water uptake, but also show a good adhesion to enamel and/or dentin.

The enamel adhesion of the inventive dental composition can be in the range of about 2 to about 15 MPa, or in the range of about 5 to about 13 MPa, or in the range of about 7 to about 12 MPa, measured as described below.

The dentin adhesion of the inventive dental composition can be in the range of about 2 to about 10 MPa, or in the range of about 4 to about 8 MPa, or in the range of about 5 to about 7 MPa, measured as described below.

The contact angle versus deionized water of the inventive dental composition can be above about 5°, or above about 10°, or above about 15° if the composition is cured in the presence of air, measured as described below.

If the composition is cured in the absence of air, the contact angle versus deionized water of the inventive dental composition can be above about 30°, or above about 40°, or above about 50°, measured as described below.

Examples of phosphoric acid esters bearing substituents with one ethylenically unsaturated moiety on the phosphorus atom according to component (a) include, but are not limited to 2-methacryloyloxyethyl phosphate, 2-methacryloyloxypropyl phosphate, 3-methacryloyloxypropyl phosphate, 2-methacryloyloxybutyl phosphate, 3-methacryloyloxybutyl phosphate, 4-methacryloyloxybutyl phosphate, 5-methacryloyloxy-3-oxa-pentyl phosphate, bis(2-methacryloyloxyethyl) phosphate, bis(2-methacryloyloxypropyl) phosphate, bis(3-methacryloyloxypropyl) phosphate, bis(2-methacryloyloxybutyl) phosphate, bis(3-methacryloyloxybutyl) phosphate, bis(4-methacryloyloxybutyl) phosphate, bis(5-methacryloyloxy-3-oxa-pentyl) phosphate or mixtures thereof.

Examples of phosphoric acid esters bearing substituents with two or more ethylenically unsaturated moieties on the phosphorus atom according to component (b) include, but are not limited to glycerol-1,3-dimethacrylate-2-phosphate, glycerol-1,2-dimethacrylate-3-phosphate, bis(glycerol-1,3-dimethacrylate) phosphate, bis(glycerol-1,2-dimethacrylate) phosphate, (glycerol-1,2-dimethacrylate)(glycerol-1,3-dimethacrylate) phosphate, (trimethylolpropane dimethacrylate) phosphate, bis(trimethylolpropane dimethacrylate) phosphate, (trimethylolethane dimethacrylate) phosphate, bis(trimethylolethane dimethacrylate) phosphate, pentaerythritol trimethacrylate phosphate or mixtures thereof.

Initiators according to component (c) are photoinitiator systems for free radical polymerization known to the person skilled in the art dealing with dental materials. Typical examples are combinations of a sensitizing agent with a reducing agent.

As the sensitizing agent, those which can polymerize the polymerizable monomer by the action of a visible light having a wavelength of from 390 nm to 830 nm are preferred. Examples thereof include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone, acyl phosphine oxides such as (2,4,6-trimethylbenzoyl)diphenylphosphine oxide, and azide-containing compounds. These compounds may be used singly or in admixture.

As the reducing agent, tertiary amines and the like are generally used. Suitable examples of the tertiary amines include N,N-dimethyl-p-toluldine, N,N-dimethylaminoethyl methacrylate, triethanolamine, methyl 4-dimethylaminobenzoate, ethyl 4-dimethylaminobenzoate, and isoamyl 4-dimethylaminobenzoate. As other reducing agents, sodium sulfinate derivatives and organometallic compounds can also be used. These compounds may be used singly or in admixture.

Further examples of suitable initiator systems can be found in the literature, e.g. J.-P. Fouassier, Photoinitiation, Photopolymerization, and Photocuring, Hanser Publishers, Munich, Vienna, New York, 1995, and J.-P. Fouassier, J. F. Rabek (eds.), Radiation Curing in Polymer Science and Technology, Vol. II, Elsevier Applied Science, London, New York, 1993.

Moreover, ternary photopolymerization initiating systems consisting of a sensitizer, an electron donor and an onium salt as described in U.S. Pat. Nos. 6,187,833, 6,025,406, 6,043,295, 5,998,495, 6,084,004 and U.S. patent application Ser. No. 10/050,218 can be used and are included herein by reference.

Examples of stabilizers according to component (d) are butylated hydroxytoluene (BHT), hydroquinone, hydroqulnone monomethyl ether (MEHQ), 3,5-di-tert-butyl-4-hydroxyanisole (2,6-di-tert-butyl-4-ethoxyphenol), 2,6-di-tert-butyl4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy4-methoxybenzophenone (UV-9), 2-(2'-hydroxy-4',6'-di-tertpentylphenyl)-2H-benzotriazole, 2-hydroxy-4-n-octoxybenzophenone, and 2-(2'-hydroxy-5'-methacryloxyethylphenyl)-2H-benzotriazole. Such adjuvants may optionally comprise reactive functionality so that they will be copolymerized with the resin.

Examples of unsaturated monomers according to component (e) are ethylene glycol di(meth)acrylate, diethylene glycol di(meth)acrylate, triethylene glycol di(meth)acrylate, tetraethylene glycol di(meth)acrylate, polyethylene glycol di(meth)acrylate, 1,3-butylene glycol di(meth)acrylate, 1,6-hexane diol di(meth)acrylate, neopentyl glycol di(meth)

acrylate, tripropylene glycol di(meth) acrylate, polypropylene glycol di(meth)acrylate, glycerol di(meth)acrylate, bisphenol A di(meth)acrylate, bisphenol A glycidyl di(meth) acrylate, bisphenol A propyl di(meth)acrylate, bisphenol A isopropyl di(meth)acrylate, ethylene oxide modified bisphenol A di(meth)acrylate, ethylene oxide modified bisphenol A glycidyl di(meth)acrylate, 2,2-bis(4-methacryloxypropoxyphenyl) propane, 7,7,9-trimethyl-4,13-dioxy-3,14-dioxa-5,12-diazahexadecane-1,16-diol di(meth)acrylate, neopentyl glycol hydroxypivalic acid ester di(meth)acrylate, caprolactone modified hydroxypivalic acid neopentyl glycol ester di(meth)acrylate, trimethylol ethane di(meth)acrylate, trimethylol propane di(meth)acrylate, trimethylol methane tri(meth)acrylate, trimethylol ethane tri(meth)acrylate, trimethylol propane tri(meth)acrylate, pentaerythritol tri(meth) acrylate, dipentaerythritol tri(meth)acrylate, pentaerythritol tetra(meth)acrylate, dipentaerythritol tetra(meth)acrylate, dipentaerythritol hexa(meth)acrylate, the reaction product of 3-chloro-2-hydroxypropyl (meth)acrylate and methylcyclohexane diisocyanate, the reaction product of 2-hydroxypropyl (meth)acrylate and methylcyclohexane diisocyanate, the reaction product of 2-hydroxypropyl (meth)acrylate and methylene bis (4-cyclohexylisocyanate), the reaction product of 2-hydroxypropyl(meth)acrylate and trimethylhexamethylene diisocyanate, the reaction product of 2-hydroxyethyl (meth)acrylate and isophorone diisocyanate, and the reaction product of 3-chloro-2-hydroxypropyl (meth)acrylate and isophorone diisocyanate, methyl (meth)acrylate, ethyl (meth) acrylate, propyl methacrylate, isopropyl methacrylate, n-butyl (meth)acrylate, iso-butyl (meth)acrylate, 2-ethylhexyl (meth)acrylate, lauryl (meth)acrylate, tridecyl (meth)acrylate, stearyl (meth)acrylate, cyclohexyl (meth)acrylate, benzyl (meth)acrylate, 2-hydroxyethyl (meth)acrylate, 2-hydroxypropyl (meth)acrylate, glycidyl (meth)acrylate, tetrahydrofurfuryl (meth)acrylate, allyl (meth)acrylate, 2-ethoxyethyl (meth)acrylate, methoxydiethylene glycol (meth)acrylate, methoxytetraethylene glycol (meth)acrylate, methoxypolyethylene glycol (meth)acrylate, phenoxy-diethyleneglycol (meth)acrylate, phenoxyhexaethyleneglycol (meth)acrylate, glycerol (meth)acrylate, tetrahydrofurfuryl (meth)acrylate, dicyclopentenyl (meth)acrylate, isobornyl (meth)acrylate, phenyl (meth)acrylate, pentaerythritol mono (meth)acrylate, dipentaerythritol mono(meth)acrylate, and mixtures thereof.

Examples of polymers according to component (f) are (meth)acrylate functionalized copolymers of acrylic acid, (meth)acrylic acid, maleic acid, and itaconic acid as described e.g. in EP 0 323 120 A1. This document is explicitly mentioned and its disclosure, especially the disclosure relating to the preparation of (meth)acrylate functionalized copolymers of acrylic acid, (meth)acrylic acid, maleic acid, and itaconic acid disclosed in the above mentioned location, is regarded as being part of the disclosure of the present invention.

Examples of prepolymers according to component (f) are especially described in WO 01/44338 A1. This document is explicitly mentioned also and its disclosure, especially the disclosure relating to the preparation of unsaturated urethane prepolymers disclosed in the above mentioned location, is regarded as being part of the disclosure of the present invention. The prepolymers preferably do not contain hydroxy, acidic or ionic groups.

The urethane prepolymers as a preferred example for the unsaturated prepolymers according to component (f) can be obtained by reaction of (A) 15 to 85 wt.-% of one ore more α, ω-terminated poly(meth)acrylate diols, (B) 0 to 30 wt.-% of one or more radically curable, polyhydroxy-functional compounds, (C) 14 to 60 wt.-% of one ore more polyisocyanates, (D) 1 to 40 wt. % or a monofunctional compound, reactive vis-à-vis isocyanate groups, which contain one or more radically curable groupings.

The prepolymers obtained can have an average molecular weight (Mw) according to GPC measurements against polystyrene standards in the range between about 400 and about 200.000 g/mol, or between about 500 and about 100.000 g/mol or between about 600 and about 20.000 g/mol.

Examples of solvents according to component (g) are water, linear, branched or cyclic, saturated or unsaturated alcohols with 2 to 10 C atoms, ketones, esters or mixtures of two or more of said type of solvents.

Especially preferred alcoholic solvents are methanol, ethanol, iso-propanol and n-propanol.

Other suitable organic solvents are THF, acetone, methylethyl ketone, cyclohexanol, toluene, alkanes and acetic acid alkyl esters, in particular acetic acid ethyl ester.

Generally, it is possible to use the above-mentioned solvents alone or as a mixture of two or more of any of these solvents, if the solvent mixtures do not impair the adhesive properties to such an extent that the desired result cannot be obtained.

Examples of a fluoride release agent according to component (h) are naturally occuring or synthetic fluoride minerals such as sodium fluoride, fluoride glass such as fluoroaluminosilicate glass, simple and complex inorganic fluoride salts such as potassium zinc fluoride and potassium hexa fluorotitanate, simple and complex organic fluoride salts such as tetra ethyl ammonium tetra fluoroborate or combinations thereof. Optionally these fluoride sources can be treated with surface treatment agents. In certain instances, the fluoride source and the filler (i) can be one and the same.

Examples of a nonreactive inorganic filler according to component (i) are naturally-occurring or synthetic materials such as quartz, nitrides (e.g., silicon nitride), glasses derived from, for example Ce, Sb, Sn, Zr, Sr, Ba or Al, colloidal silica, feldspar, borosilicate glass, kaolin, talc, titania, and zinc glass, zirconia-silica fillers; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa, and "Cab-O-Sil M5" silica sold by Cabot Corp.). Preferred filler particles are quartz, submicron silica, and non-vitreous microparticles of the type described in U.S. Pat. No. 4,503,169. Mixtures of these fillers are also contemplated, as well as combination fillers made from organic and inorganic materials.

Optionally, the surface of the filler particles may be treated with a surface treatment, such as a silane coupling agent, in order to enhance the bond between the filler and the polymerizable resin. The coupling agent may be functionalized with reactive curing groups, such as acrylates and/or methacrylates.

Examples of a photobleachable colorant according to component (j) are Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725 and are included herein by reference. The color of the compositions of the present invention may be additionally imparted by a sensitizing compound.

The dental composition of the invention does not necessarily comprise halogenated solvents and/or solvents with a boiling point larger than 150° C., intensely colored dyes or pigments which are not photobleachable, fillers with an average particle size larger than 50 μm, aldehydes, and/or monomers with free carboxylic acid groups.

The phosphoric acid esters (a) mentioned above usually do not comprise alkylene chains with more than four carbon atoms. The phosphoric acid esters (b) mentioned above usually do not comprise residues $R_3$, $R_4$, or $R_5$ with more than 15 carbon atoms. The phosphoric acid esters (a) and (b) mentioned above usually do not comprise phosphoric acid aryl esters which do not bear ethylenically unsaturated moieties on the aryl substituent.

These dental adhesive compositions can be used for the adhesive securing of dental filling materials based on methacrylates and epoxies, as self-adhesive dental pit and fissure sealants, and as self-adhesive dental desensitizers.

Suitable dental filling materials based on methacrylates are described e.g. in WO 01/30305 A1, WO 01/30306 A1, WO 01/30307 A1.

Suitable dental filling materials based on epoxies are described e.g. in U.S. Pat. Nos. 6,254,828, 6,084,004, WO 01/51540 A1, WO 02/66535 A1, WO 98/47046 A1, WO 98/47047 A1.

These dental adhesive compositions are especially useful for adhesive securing of dental filling materials based on epoxies as described in WO 01/51540 A1 on pages 18-19. The above mentioned documents are explicitly mentioned, and their disclosure is regarded as being part of the disclosure of the present invention.

The dental composition of the invention provides at least comparable adhesion values to state of the art self-adhesive dental materials. In addition they exhibit a significant decrease in polarity upon polymerization and are therefore less prone to hydrolysis, swelling and leakage of monomers. They exhibit also improved film forming properties on dental hard tissue, especially on dentin, along with a reduced hydrophilicity.

If applied for the adhesive securing of dental filling materials, these compositions ensure a better wetting of the filling material during application, and therefore an easier handling and better marginal adaptation.

The inventive composition is usually applied to the tooth surface in an amount sufficient to etch and prime the dental tissue. In this respect the following steps are applied:
  a) applying the composition to the surface of a tooth (enamel and/or dentin), preferably using a brush or a sponge,
  b) optionally dispersing the composition to a thin film, preferably using a stream of air,
  c) light or redox initiated curing of the composition,
  d) optionally applying a dental filling composition.

The composition of the present invention can be provided as a kit of parts comprising at least two parts.

The composition can generally be provided in any type of package, e.g. tubes, or flasks. For the application of small amounts of liquids, however, the prior art discloses a number of alternatives which facilitate the application.

For dental application, multi chamber packaging devices as described in EP 0 895 943 B1, WO-02/38468 A1, WO 01/58869 A1 are preferred.

Therefore, the present invention also relates to a kit of parts, comprising at least two parts, wherein in one part preferably components (a), (b), (c), optionally (d), (e), optionally (f), optionally (h), optionally (i), optionally (j) and in another part components (c), optionally (d), (e), optionally (f), optionally (g) as described above are comprised. The partitioning of the components should prevent undesired reactions of the composition. Components comprising OH groups should preferably stored in one part, phosphoric acid esters (a) and (b) in the other part.

The composition of the present invention usually is prepared by mixing the components, e.g. by stirring or shaking.

The following experiments and results are provided to exemplify the invention, without limiting the scope of the invention.

Abbreviations:
PM2 mixture of reaction products of 2-hydroxyethyl methacrylate (HEMA) with phosphorus pentoxide, commercially available from Nippon Kayaku as Kayamer PM2
PGDMA mixture of reaction products of glycerol di(methacrylate) (GDMA) with phosphorus pentoxide
HEMA hydroxyethyl methacrylate
UDMA urethane dimethacrylate
PUMA step growth polymerization product of Tego Diol BD-1000, TMHDI, and HEMA (preparative example 2 of WO 01/44338 A1)
BisGMA bisphenol A diglycidyl methacrylate
CPQ camphorquinone
EDMAB ethyl 4-dimethylaminobenzoate
MEHQ hydroquinone monomethyl ether
BHT butylated hydroxytoluene If not otherwise indicated, the term "parts" means "parts by weight".

PREPARATIVE EXAMPLE 1

A liquid was prepared by combining PGDMA (40.0 parts), PM2 (19.1 parts), HEMA (12.0 parts), UDMA (10 parts), ethoxylated bisphenol A dimethacrylate (8.0 parts), deionized water (6.0 parts), BisGMA (2.0 parts), CPQ (1.6 parts), EDMAB (1.2 parts), MEHQ (0.05 parts), and BHT (0.05 parts).

The adhesion measurement on bovine teeth by adhesive securing of a filling material with this liquid was performed by a tensile bond strength test as described in U.S. Pat. No. 6,245,872 or WO 01/10388:

Five freshly extracted bovine teeth were ground down by abrasive paper to the point where a sufficiently large exposed enamel or dentine surface resulted. In each case, small wax discs with a 6 mm punched-out hole were glued onto these surfaces in order to obtain a standardized adhesion surface. The liquid was applied to the entire surface and rubbed in with moderate finger pressure for 20 seconds by means of a microbrush. Compressed air was then blown on briefly until a thin liquid film with a smooth glossy surface was obtained. Then the film was polymerized by application of a light polymerization apparatus (Elipar Trilight, 3M ESPE, light intensity: approx. 800 W/cm$^2$) for 10 seconds. Then, a dental filling material was introduced in two layers into the recesses of the small wax discs and each layer was thoroughly polymerized in accordance with the manufacturers instructions. The small wax discs were removed and the specimens were stored for 24 hours at 36° C. and 100% humidity. Finally, the test pieces were pulled off in a tensile test (Zwick Universal testing machine). The enamel and dentin adhesion values obtained are shown in Table 1.

The decrease in polarity upon polymerization of this material was examined as follows:

A thin film of the liquid was prepared on a glass slide and polymerized as described above in the presence of air. A 5 μl droplet of deionized water was placed on the inhibition layer of the polymerized film, and the contact angle was observed by means of a contact angle microscope (Krüss DSA 10). After 5 seconds, a contact angle of 21° was measured. A second specimen was prepared by polymerizing the liquid under a polystyrene film in the absence of air. For this specimen, a much larger contact angle of 55° was observed indicating a significant decrease in polarity of the material upon polymerization.

PREPARATIVE EXAMPLE 2

A liquid was prepared by combining PGDMA 40.0 parts, PM2 19.1 parts, HEMA 12.0 parts, PUMA 10 parts, ethoxylated bisphenol A dimethacrylate 8.0 parts, DI water 6.0 parts, BisGMA 2.0 parts, CPQ 1.6 parts, EDMAB 1.2 parts, MEHQ 0.05 parts, and BHT 0.05 parts.

For all specimens, a smooth and glossy surface on both enamel and dentin was observed for the polymerized film of the adhesive before application of the dental filling material.

Adhesive securing of an epoxy based composite filling material as described in WO 01/10388, page 12, was performed according to the method described in Preparative Example 1. The adhesion values for enamel and dentine are given in Table 1.

For polymerized films of this liquid, contact angles versus deionized water were 21° for a specimen prepared in the presence of air, and 54° for a specimen prepared in the absence of air.

REFERENCE EXAMPLE 1

A liquid was prepared by combining PGDMA (59.1 parts), HEMA (12.0 parts), UDMA (10 parts), ethoxylated bisphenol A dimethacrylate (8.0 parts), deionized water (6.0 parts), BisGMA (2.0 parts), CPQ (1.6 parts), EDMAB (1.2 parts), MEHQ (0.05 parts), and BHT (0.05 parts).

Adhesive securing of an epoxy based composite filling material as described in WO 01/10388, page 12, was performed according to the method described in Preparative Example 1. The adhesion values for enamel and dentine are given in Table 1.

For polymerized films of this liquid, contact angles versus deionized water were 22° for a specimen prepared in the presence of air, and 54° for a specimen prepared in the absence of air.

REFERENCE EXAMPLE 2

A liquid was prepared by combining PM2 (59.1 parts), HEMA (12.0 parts), UDMA (10 parts), ethoxylated bisphenol A dimethacrylate (8.0 parts), deionized water (6.0 parts), BisGMA (2.0 parts), CPQ (1.6 parts), EDMAB (1.2 parts), MEHQ (0.05 parts), and BHT (0.05 parts).

Adhesive securing of an epoxy-based composite filling material as described in WO 01/10388 was performed according to the method described in Preparative Example 1. The adhesion values for enamel and dentine are given in Table 1.

For polymerized films of this liquid, a contact angle versus deionized water of less than 5° was observed for specimens polymerized in the presence and in the absence of air.

TABLE 1

| | Example | Filling material | Enamel adhesion [MPa] | Dentine adhesion [MPa] |
|---|---|---|---|---|
| A | Prep. Example 1 | epoxy-based composite | 8.9 | 3.8 |
| B | Prep. Example 1 | Filtek ™ Z250 | 8.3 | 5.0 |
| C | Prep. Example 1 | Filtek ™ Supreme | 8.2 | 4.5 |
| D | Prep. Example 2 | epoxy-based composite | 8.2 | 4.1 |
| E | Ref. Example 1 | epoxy-based composite | 4.1 | 3.4 |
| F | Ref. Example 2 | epoxy-based composite | 6.2 | 2.7 |

The values given are the average of five measurements each.

The epoxy-based composite material is described in WO 01/10388 A1, page 12. Filtek™ Z250 and Filtek™ Supreme are commercially available from 3M ESPE AG.

In order to exemplify the low-polar nature of the inventive compositions, while providing good adhesion to the tooth, the water uptake has been determined for three compositions described in the application.

Five specimens (15 mm diameter, 1 mm height) of each of the respective compositions were prepared in accordance with DIN EN ISO 4049. The specimens were weighed and then immersed in water at 37° C. After 5 h, the specimens were weighed again. The increase in weight for the different compositions, and the adhesion to enamel is shown in the table below. The method for measuring the adhesive strength is described in the patent application.

TABLE 2

| Composition | water uptake in wt-% after 5 h | Enamel adhesion |
|---|---|---|
| Preparative Example 2 | 3.6 | 8.2 |
| Reference Example 1 | 1.5 | 4.1 |
| Reference Example 2 | 10.6 | 6.2 |

After 5 h, no further significant changes in the weight of the specimens were detected.

The invention claimed is:

1. A dental composition comprising:
   a) at least one phosphoric acid ester having at least one substituent with one ethylenically unsaturated moiety, wherein the substituent is bonded to the phosphorous atom;
   b) at least one phosphoric acid ester having at least one substituent with two or more ethylenically unsaturated moieties, wherein the substituent is bonded to the phosphorous atom;
   c) at least one initiator; and
   d) an additional component selected from unsaturated monomers and unsaturated prepolymers;
   wherein component (b) is present in the composition in an amount of about 150 to about 250 parts by weight based on about 100 parts by weight of component (a).

2. The dental composition of claim 1, further comprising an additive selected from the group consisting of stabilizers, unsaturated polymers, solvents, fluoride release agents, non-reactive inorganic fillers, and photobleachable colorants.

3. The dental composition according to claim 1, wherein component (a) is represented by formula (I)

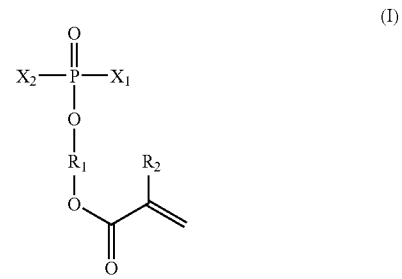

wherein $R_1$ is selected from the group consisting of (i) an alkylene having 1 to 4 C atoms, (ii) or a bivalent organic group having 1 to 4 carbon atoms composed of two or more hydrocarbon residues bonded to one another by one or more ether or thioether linkages, and (iii) or an aryl, each optionally substituted with OH;
wherein $R_2$ is H, or $CH_3$;
wherein $X_1$ is OH or halogen; and
wherein $X_2$ is $X_1$ or —O—$R_1$—OOC—$CR_2$=$CH_2$, and component (b) is represented by formula (II),

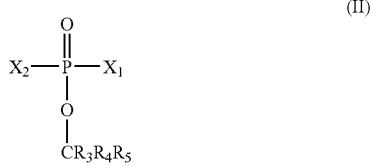

wherein $R_3$, $R_4$, and $R_5$ are independently selected from (i) H, (ii) linear or branched alkyl groups having 1 to 4 carbon atoms, optionally substituted with OH, (iii) aryl groups, optionally substituted with OH, and (iv) organic groups having 5 to 15 carbon atoms composed of 2 to 6 saturated or ethylenically unsaturated hydrocarbon residues bonded to one another by one or more ether, thioether, ester, thioester, thiocarbonyl, amide, urethane, carbonyl and/or sulfonyl linkages, each optionally substituted with OH,
wherein at least 2 of the groups $R_3$, $R_4$, and $R_5$ comprise at least 1 group according to formula (III)
or
at least 1 of the groups $R_3$, $R_4$, and $R_5$ comprises at least 2 groups according to formula (III)

and wherein $X_2$=$X_1$ or —O—$CR_3R_4R_5$ or —O—$R_1$—OOC—$CR_2$=$CH_2$.

4. The dental composition according to claim 1, wherein the total amount of components (a) and (b) in the composition is about 10 to about 90 parts by weight.

5. The dental composition according to claim 1, wherein the prepolymer is present in an amount of about 0 to about 30 parts by weight.

6. The dental composition according to claim 5, wherein the prepolymer does not contain any hydroxy, acidic or ionic groups.

7. The dental composition according to claim 5, wherein the prepolymer has an Mw in the range of about 600 to about 20000.

8. The dental composition according to claim 1 having a contact angle versus deionized water of more than 15°, if the composition is cured in the presence of air, and of more than 50°, if the composition is cured in the absence of air.

9. The dental composition according to claim 1 having an adhesion to enamel and/or dentin in the range of about 2 to about 15 MPa.

10. The dental composition according to claim 1 having a water uptake of less than 5% by weight with respect to the cured composition measured after having immersed the composition for 5 h in water of 37°C.

11. The dental composition according to claim 9 having an enamel adhesion of at least 5 MPa.

12. The dental composition according to claim 1, wherein component (a) is selected from the group consisting of 2-methacryloyloxyethyl phosphate, 2-methacryloyloxypropyl phosphate, 3-methacryloyloxypropyl phosphate, 2-methacryloyloxybutyl phosphate, 3-methacryloyloxybutyl phosphate, 4-methacryloyloxybutyl phosphate, 5-methacryloyloxy-3-oxa-pentyl phosphate, bis(2-methacryloyloxyethyl) phosphate, bis(2-methacryloyloxypropyl) phosphate, bis(3-methacryloyloxypropyl) phosphate, bis(2-methacryloyloxybutyl) phosphate, bis(3-methacryloyloxybutyl) phosphate, bis(4-methacryloyloxybutyl) phosphate, bis(5-methacryloyloxy-3-oxa-pentyl) phosphate, and mixtures thereof.

13. The dental composition according to claim 1, wherein component (b) is selected from the group consisting of glycerol-1,3-dimethacrylate-2-phosphate, glycerol-1,2-dimethacrylate-3-phosphate, bis(glycerol-1,3-dimethacrylate) phosphate, bis(glycerol-1,2-dimethacrylate) phosphate, (glycerol-1,2-dimethacrylate), (glycerol-1,3-dimethacrylate) phosphate, (trimethylolpropane dimethacrylate) phosphate, bis(trimethylolpropane dimethacrylate) phosphate, (trimethylolethane dimethacrylate) phosphate, bis(trimethylolethane dimethacrylate) phosphate, pentaerythritol trimethacrylate phosphate and mixtures thereof.

* * * * *

UNITED STATES PATENT AND TRADEMARK OFFICE
CERTIFICATE OF CORRECTION

PATENT NO. : 7,700,668 B2
APPLICATION NO. : 10/564101
DATED : April 20, 2010
INVENTOR(S) : Christoph Thalacker et al.

It is certified that error appears in the above-identified patent and that said Letters Patent is hereby corrected as shown below:

Title page
Item [56], References Cited, U.S. PATENT DOCUMENTS, please add the following reference that was cited by the Examiner but does not appear on the printed patent
-- 2003/0199605 10-2003 Fischer, Dan E. 523/116 --.

Column 1
Line 9, delete "an decrease" and insert -- a decrease --, therefor.

Column 6
Line 30, delete "toluldine," and insert -- toluidine, --, therefor.
Lines 50-51, delete "hydroqulnone" and insert -- hydroquinone --, therefor.
Line 53, delete "butyl4-" and insert -- butyl-4- --, therefor.

Column 10
Line 54, delete "manufacturers" and insert -- manufacturer's --, therefor.

Signed and Sealed this
Twenty-eighth Day of December, 2010

David J. Kappos
*Director of the United States Patent and Trademark Office*